United States Patent [19]

Kramer

[11] Patent Number: 4,634,117

[45] Date of Patent: Jan. 6, 1987

[54] LUNG TRAINER

[76] Inventor: Peter G. Kramer, R.D. #3 Box 4720, Morrisville, Vt. 05661

[21] Appl. No.: 649,925

[22] Filed: Sep. 13, 1984

[51] Int. Cl.⁴ .............................................. A63B 23/00
[52] U.S. Cl. ...................................... 272/99; 128/914; 128/201.26
[58] Field of Search ...................... 272/99; 128/201.11, 128/201.24, 201.26, 270.16, 914, 201.13, 203.28

[56] References Cited

U.S. PATENT DOCUMENTS

| Re. 25,122 | 2/1962 | Page | 128/207.16 X |
| 2,975,439 | 3/1961 | Bentley | 128/201.11 X |
| 3,265,066 | 8/1966 | Katehis | 128/201.11 |
| 4,138,105 | 2/1979 | Hunger et al. | 272/99 |
| 4,143,872 | 3/1979 | Havstad et al. | 272/99 |
| 4,230,106 | 10/1980 | Geeslin et al. | 128/201.11 |
| 4,334,533 | 6/1982 | Henkin | 128/914 X |

Primary Examiner—Robert A. Hafer
Assistant Examiner—Kathleen D'Arrigo
Attorney, Agent, or Firm—Limbach, Limbach & Sutton

[57] ABSTRACT

An apparatus for increasing the respiratory tidal volume of athletes is described. The invention provides additional volume to the anatomical dead space requiring the athlete to ventilate at a higher rate than that dictated by the actual work or training being done. This results in a respiratory effort in excess of the respiratory requirement.

2 Claims, 3 Drawing Figures

U.S. Patent  Jan. 6, 1987  4,634,117
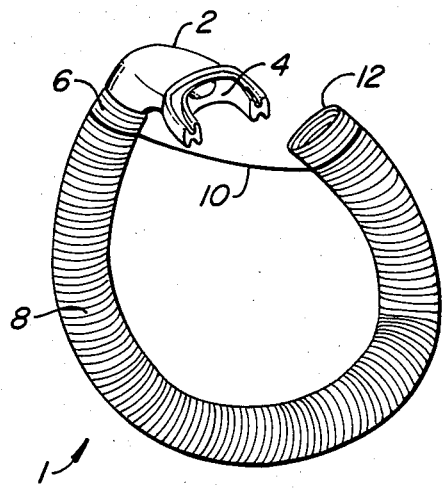
FIG._1.
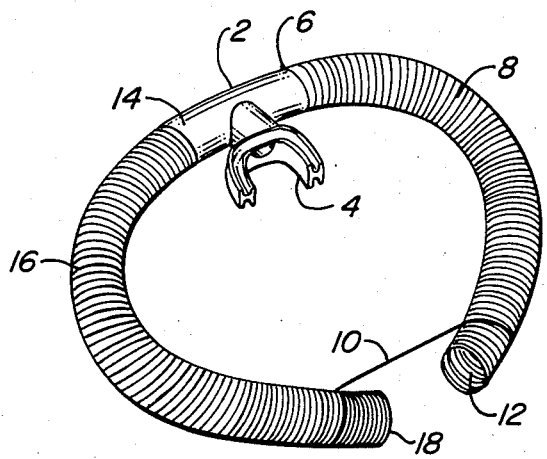
FIG._2.
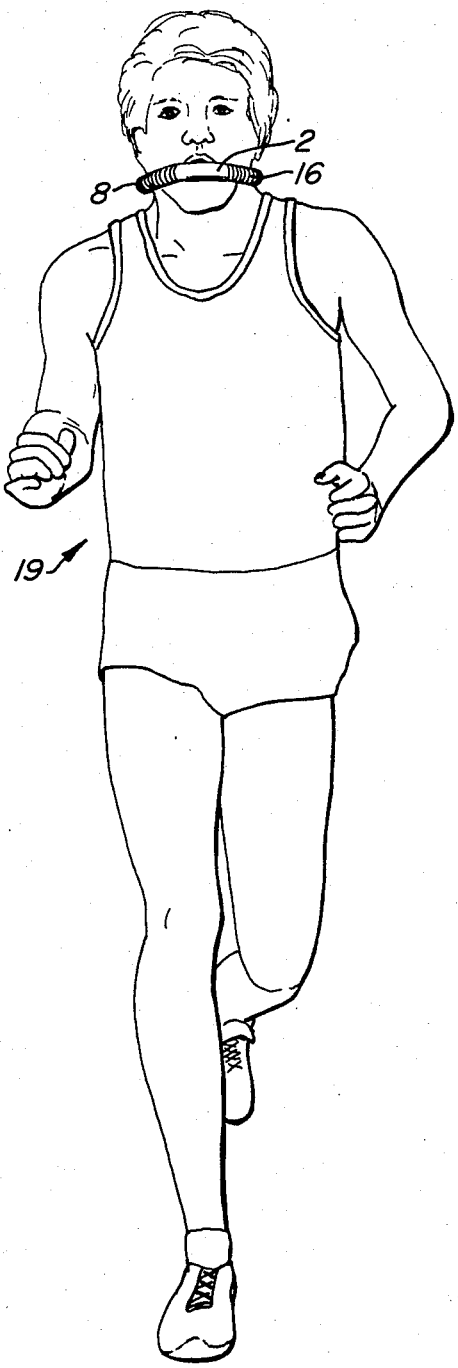
FIG._3.

4,634,117

LUNG TRAINER

TECHNICAL FIELD

This invention relates to an apparatus and method used to develop the respiratory capacity of endurance athletes.

BACKGROUND ART

There appears to be two mechanisms involved in controlling the respiratory response of an individual when he is engaged in exercise. The first mechanism is a neural mechanism. There are nerve receptors in working tissues which increase their frequency of firing when an individual engages in physical activity. This increase in neurological activities causes an increase in the respiratory effort of the individual in both rate and tidal volume. This neural mechanism works at the moment exercise begins. A second mechanism appears to modify the respiratory response in a slow manner; this is a humoral mechanism. Chemical changes in the blood, to include changes in the oxygen and carbon dioxide content and the hydrogen ion concentration will affect the individual's respiratory response. Many athletes state that one of the greatest difficulties they experience between training and racing is the perception that they can feel their increased respiratory effort, yet are still unable to get sufficient amounts of air.

The anatomical dead space is the quantity of air which can be found in the mouth, throat, trachea, main stem bronchi, and the large bronchioles of the lungs. The gas contained in the anatomical dead space does not participate in the diffusion resulting in blood-born oxygen. Increasing the anatomical dead space over a period of a few minutes creates subtle changes in the blood causing an increased respiratory effort on the part of the athlete. By enlarging the anatomical dead space, the individual's respiratory effort will exceed the respiratory requirement of the particular work load he is using in his training.

An earlier method for increasing the respiratory rate utilized a gas mixture with sub-atmospheric oxygen levels. The user would respire through a scuba-type device connected to a gas cylinder. This method has several disadvantages for use during strenuous exercise. The apparatus is bulky and cumbersome. Also, a supplier of the gas composition would be difficult to locate.

Many of the other devices utilized in improving respiratory effort and response were developed for therapeutic use by victims of respiratory ailments.

In U.S. Pat. No. 3,455,294 (Adler) a device is described for use in the treatment of patients suffering from pneumonia and varying forms of pneumonitis. The object of the Adler device is to increase carbon dioxide inhalation by the patient. This stimulates the individual to breathe deeper. An increase in the tidal volume of the patient often results in effective coughing to clear the lung of bronchial obstruction with mucous. The device itself consists of a series of cup-shaped internal chambers contained within a larger chamber. Such members are positioned to provide a tortuous pathway for respiration. Patients are advised to use the device for 3 to 5 minutes at hourly intervals. The Adler patent also describes means for injecting medicaments into the device to facilitate respiration.

This invention provides several advantages over the prior art. This device is easy to use. Its simplicity makes it more attractive to the user. There are no gas cylinders to attend to, nor suppliers of the right oxygen poor composition to locate. This invention is also more suited to use by athletes in training than the device described in U.S. Pat. No. 3,455,294. The Adler device is not designed for use at higher repiration rates nor during strenuous activity. There are no means provided to clamp the device securely to the mouth. The invention herein disclosed provides a light weight and unobtrusive means to facilitate endurance training. Specifically, this device is worn by endurance athletes during their training sessions to prepare their respiratory mechanism for competition.

It is therefore an object of this invention to force the respiratory system to work and ventilate at a higher rate than that dictated by the actual work or training being done.

It is a further object of this invention to provide a means for accomplishing this increased respiratory response which is flexible and light weight and can be worn without distracting the athlete from his training.

DISCLOSURE OF THE INVENTION

The apparatus in accordance with this invention is comprised of three basic parts: flexible tubing allowing an air volume ranging from 500–1000 ml, a soft mouthpiece made of rubber, and surgical tubing to attach to both ends of the flexible tubing to give it its U-shape. The device is worn around the neck with the mouthpiece inserted in the athlete's mouth. The tubing is light weight and flexible and can be shaped into a modified U. The mouthpiece is made of soft rubber which can be placed over one of the ends of the flexible tubing.

BRIEF DESCRIPTION OF THE DRAWINGS

FIG. 1 shows a top perspective view of one embodiment of the invention.

FIG. 2 shows a perspective view of another embodiment of the invention.

FIG. 3 shows a view of the apparatus of the present invention in use.

BEST MODE FOR CARRYING OUT THE INVENTION

The physiological principles on which the invention works are simple. Each time an athlete inhales or exhales that air has a volume known as the tidal volume. Tidal volume is divided into two parts. The most important and largest part is known as the alveolar volume. This is the air which enters deep into the respiratory system in the area of the terminal bronchioles and alveoli; it is the gas that participates in the diffusion between the respiratory and circulatory systems. The second portion of the tidal volume is known as the anatomical dead space. This is the quantity of air which can be found in the mouth, throat, trachea, main stem bronchi, and the large bronchioles of the lungs. This gas does not participate in diffusion.

The anatomical dead space varies between individuals; however, it is generally accepted that an individual's anatomical dead space is approximately 1 ml per pound of body weight. It can be assumed that a 150 pound athlete has approximately 150 ml of anatomical dead space. During exercise, to facilitate the rapidity of the flow of gas from the atmosphere to the alveolar section of the lungs, the anatomical dead space of an athlete actually increases due to the dilation of those large conducting tubules. It is believed that during strenuous exercise, the anatomical dead space in an athlete is approximately twice its resting value. Therefore, it would not be unrealistic to expect that an exercising 150 pound athlete could have a functional anatomical dead space of approximately 300 mls. In one embodiment of the invention, referring now to FIG. 1, the lung trainer 1 is comprised of three parts. A soft rubber mouthpiece 2 has a section 4 which is placed in the athlete's mouth. The other end 6 of the mouthpiece 2 fits snugly inside one end of the flexible tube 8. Flexible tube 8 preferably has a diameter of 3 centimeters and its length varies between 70 and 140 centimeters. This allows for an air volume ranging between 500 to 1000 mls. The tube is flexible and light weight and can be bent into a modified U-shape, such that the end 12 can be held in place by the surgical tubing 10 connected to the mouthpiece 2. The flexible tube 8 circles the neck of the athlete and returns to the front of the athlete.

Referring now to FIG. 2, in another embodiment of the invention, the mouthpiece 2 is substantially T-shaped in that section 4 is inserted in the athlete's mouth and there are two ends 6 and 14 connected with flexible tubes 8 and 16 at points 6 and 14 respectively. The flexible tubes are drawn around the athlete's neck and connected by the surgical tubing 12 at the end of each tube 18 and 10. The tubes 8 and 16 in one actual embodiment are 3 centimeters in diameter and their length varies between 35 and 70 centimeters allowing for an air volume ranging from 500 to 1000 mls.

In FIG. 3, the method of utilizing the lung trainer is demonstrated. An athlete 19 engages in strenuous effort resulting in increased heart rate, thereby requiring additional oxygen. The athlete uses the invention by inserting the mouthpiece and wrapping the flexible tubes 6 and 8 around the neck to be joined by the surgical tubing at each end of the tube. The athlete then wears the lung trainer while engaging in strenuous exercise, breathing only through the mouth, thereby increasing the respiratory capacity. An athlete using the invention described herein effectively increases his anatomical dead space between 500 to 1000 mls depending on the size of his particular training device. If the lung trainer is assumed to have a volume of 500 mls, in order to get the same amount of alveolar ventilation, an athlete using the invention will have to inspire a total of 500 mls more air per breath than he would without the device. In effect, what the invention does is to force the respiratory system to work and ventilate at a higher rate than that dictated by the actual work or training being done.

In Table I, the results of several tests performed with and without the lung trainer 1 as seen in FIG. 1. The results of these tests show that the use of the lung trainer, on the average, increased the volume of expired air by approximately 5 liters/minute, BTPS. This test was performed by monitoring both the heart rate and the volume of expired air for 9 athletes. One measurement was taken while wearing the lung trainer and the other was taken using a placebo. The placebo device enabled the athlete to respire new air each time a breath was taken. None of the athletes were told what the device was intended to do.

TABLE I

Athlete Lung Volume Expired (Units Are for Air, Liter/Min.)

| No. | Placebo | Trainer | Difference |
|-----|---------|---------|------------|
| 1 | 28.2 | 43 | 14.8 |
| 2 | 26.9 | 33.3 | 6.4 |
| 3 | 35.0 | 36.4 | 1.4 |
| 4 | 37.0 | 35.3 | −1.7 |
| 5 | 28.0 | 29.6 | 1.6 |
| 6 | 12.3 | 14.4 | 2.1 |
| 7 | 26.0 | 35.1 | 9.1 |
| 8 | 34.9 | 42.0 | 7.1 |
| 9 | 29.1 | 31.4 | 2.3 |

$$\text{Mean Diff.} = \frac{\overline{X_0} = 4.79}{2}$$

$$S = \frac{\Sigma x}{N-1} = 5.049$$

$$S_D = \frac{S}{N} = 1.68$$

$$t = \frac{X_D}{S_D} = 2.85$$

Although the foregoing invention has been described in some detail by way of illustration and example for purposes of clarity of understanding, it will be obvious to those skilled in the art that certain changes and modifications may be practiced within the scope of the appended claims.

What is claimed is:

1. An apparatus for increasing respiratory tidal volume of athletes comprising:

T-shaped mouthpiece means for respiring, having three unobstructed passages, a first passage communicating with the mouth of said athlete and comprising the vertical member of said T-shape, and second and third passages, positioned to oppose each other as the respective members of the horizontal section of said T-shape, said second and third passages easily communicating with each other and with said first passage;

two unobstructed flexible tubes, each joined at one end to said mouthpiece means at said second and third passages, and each tube open to the atmosphere at the other end to permit unobstructed inflow and outflow; and means appending the open ends of said tubes in proximity with each other, said apparatus configured such that the entire apparatus lies in substantially the same horizontal plane when in use by the athlete.

2. The apparatus of claim 1 wherein the total volume within said two tubes is between 500 ml and 1000 ml.

* * * * *